United States Patent [19]

Smernoff

[11] 4,089,748
[45] May 16, 1978

[54] MICROORGANISM GROWTH PROCESS AND CELL

[75] Inventor: Ronald B. Smernoff, Belmont, Calif.

[73] Assignee: Analytical Products, Inc., Belmont, Calif.

[21] Appl. No.: 718,101

[22] Filed: Aug. 27, 1976

[51] Int. Cl.² ............................................. C12B 1/00
[52] U.S. Cl. .................................. 195/104; 195/100; 195/102; 195/139
[58] Field of Search ................ 195/103.5 R, 104, 100, 195/102, 127, 139; 426/573, 576; 252/358

[56] References Cited

U.S. PATENT DOCUMENTS

| 2,819,970 | 1/1958 | Steigmann | 426/576 |
| 2,894,913 | 7/1959 | Sullivan et al. | 252/358 |

OTHER PUBLICATIONS

Frobisher et al., "Fundamentals of Microbiology" Saunders Co., Ninth Edition, 1974, pp. 124–128.

Primary Examiner—R. B. Penland
Attorney, Agent, or Firm—Phillips, Moore, Weissenberger, Lempio & Majestic

[57] ABSTRACT

The invention is concerned with a micro-organism growth cell comprising a sterilized container having therewithin an agar-based nutrient gel. The gel has intimately intermixed therethroughout a specific amount of a dialkylpolysiloxane which causes a top surface of the gel to be smooth insuring a uniform growth rate for a micro-organism placed upon said top surface. The invention is also concerned with a process for growing a micro-organism upon the surface of an agar-based nutrient shell at a reproducibly constant growth rate. The process comprises intermixing with agar, essential nutrients and water, sufficient of said agar being used to insure formation of a gel, prior to the gelling thereof, a specific amount of a dialkylpolysiloxane. The resulting intermixture is gelled in a sterile micro-organism growth container to form a micro-organism growth cell as described above and the top surface of the gel is innoculated with a micro-organism. The cell is incubated under preselected incubation conditions whereby the micro-organism grows at a reproducably constant growth rate upon the smooth surface of the gel.

25 Claims, 2 Drawing Figures

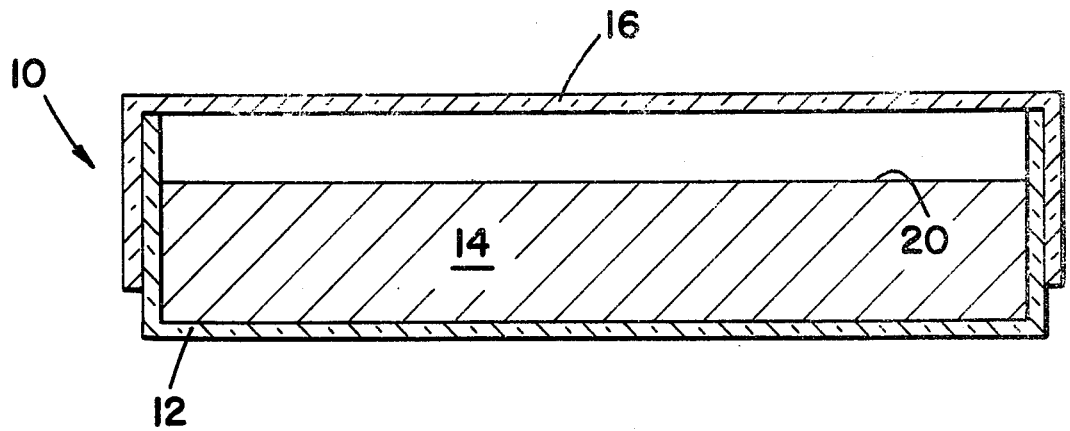
FIG_1
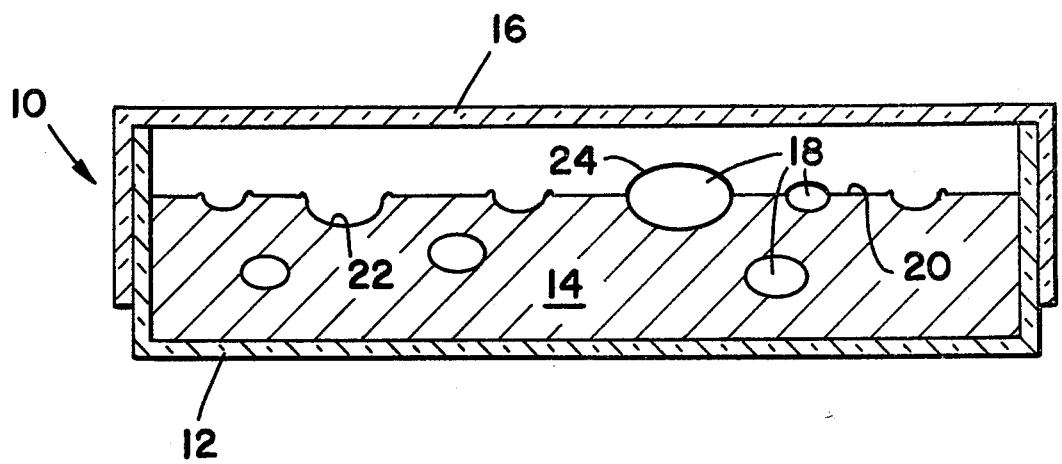
FIG_2

MICROORGANISM GROWTH PROCESS AND CELL

BACKGROUND OF THE INVENTION

1. Field of the Invention

The invention is concerned with obtaining generally reproducible growth rates for individual micro-organisms upon the surfaces of agar-based gels. More particularly, the invention is concerned with micro-organism growth upon agar-based gels which have a very smooth surface so that surface imperfections do not lead to apparent differences in growth rates of particular micro-organisms grown thereon.

2. Prior Art

The preparation of agar gels for the growth of micro-organisms so as to allow identification of the micro-organisms, identification of particularly effective anti-micro-organism agents thereagainst, and the like is of course very well known. Such agar-based gels must contain therein the essential nutrients for the growth of the particular micro-organism being grown thereon and as is well recognized must be grown in sterilized cells of one nature or another. For example, growth may take place in tubes or very often in petri dishes or the like.

A serious problem which has existed with prior art growth cells, such cells being defined as a container having an agar-based gel therein, has been that the rate of growth of a particular micro-organism on the surface of the gel has often been effected by small or large bubbles which are formed during the mixing of the materials from which the gel is formed and which do not escape fully therefrom during the gelling process. A uniform or more properly a generally reproducible growth rate is necessary for each particular micro-organism if it is to be properly identified and/or the effects of various anti-micro-organism chemicals are to be properly evaluated upon it. Heretofore, in order to obtain such a uniform rate it has been customary in the art when, for example petri dishes, are used and a gel is formed therein which does not have a completely smooth surface, to open the dishes and then quickly flame them to melt slightly the top surface thereof so that any and all depressions and/or hills therein will be smoothed out and the resulting top surface of the gel will be sufficiently smooth so that generally reproducible growth rates will be observed for each micro-organism.

This flaming solution has not proven completely satisfactory for a number of reasons. First, the flaming itself requires reopening of the petri dish or the like thus drastically increasing the chances of contamination from foreign micro-organisms. Second, the flaming is not fully effective if truly large depressions and/or hills have been introduced into the agar-based gel by the bubbles formed therein during mixing of the gel ingredients. Third, the flaming technique even when successful takes up a good deal of valuable time. Fourth, the flaming may lead to a selective destruction or removal of certain essential nutrients from the area of the gel which is directly exposed to the flame. The present invention provides a complete solution to the problem of having uneven surfaces on the top of agar-based gels while completely eliminating the necessity for flaming. This solution also removes the necessity for ever opening the petri dishes or the like which contain the gel therein except for innoculation thereof so that chances of contamination are drastically reduced. Further, the solution of the present invention to the above problems completes the formation of an agar-based gel medium on which micro-organisms will grow at precisely the same rate within experimental error as the same micro-organisms will grow upon prior art agar-based gels having smooth top surfaces as produced for example by bubble free formation of the gels. Further, by use of the technique of the present invention, much more active mixing techniques can be used to form the agar-based solution which is to be gelled thus reducing the time needed to perform such mixing.

SUMMARY OF THE INVENTION

In one sense the invention comprises a process for growing a micro-organism upon the surface of an agar-based nutrient gel at a generally reproducible growth rate. The process comprises intermixing with agar, essential nutrients and water, sufficient of said agar being used to insure formation of a gel, prior to the gelling thereof, from about 0.0008 to about 0.2 weight percent based on total gel weight of a dialkylpolysiloxane. The resulting intermixture is gelled in a stored micro-organism growth container to form a growth cell. The top surface of the gel is innoculated with a micro-organism and the cell is incubated under preselected incubation conditions to grow the micro-organism upon the smooth top surface of the gel at a generally reproducible growth rate.

In another sense the invention comprises a micro-organism growth cell. The cell comprises a sterilized container. An agar-based nutrient gel is within the container, the gel having intimately intermixed therethroughout from about 0.0008 to about 0.2 weight percent based on total gel weight of a dialkylpolysiloxane which causes a top surface of the gel to be smooth insuring a generally reproducible growth rate for a micro-organism placed upon said top surface.

BRIEF DESCRIPTION OF THE DRAWING

The invention will be better understood by reference to the figures of the drawing wherein like numbers denote like parts throughout and wherein:

FIG. 1 illustrates a micro-organism growth cell in accordance with the present invention; and FIG. 2 illustrates a micro-organism growth cell of the prior art.

DETAILED DESCRIPTION OF THE PREFERRED EMBODIMENT

The use of agar-based gels for the growing of micro-organisms such as *Escherichia coli, Salmonella typhimurium, Proteus vulgaris, Streptococcus pyogenes,* and other bacteria antihysts is so well as to need little or no description. Briefly, an agar in water solution is prepared as by dissolving the agar, generally along with any number of essential nutrients in water. The essential nutrients will generally provide sufficient nitrogen, phosphorous and various trace metals to insure proper growth of the particular micro-organism for which the growth cell is being prepared. Typically the growth cell comprises a well known petri dish or the like such as the cell 10 shown in each of FIGS. 1 and 2. As will be noted the cell 10 will generally consist of a bottom 12 which holds the agar-based gel 14 after it has set and a top 16 which fits over the bottom 12 to protect the agar-based gel 14 from contamination. The bottom 12 and the top 16 are generally sterilized prior to use in an autoclave or the like and after the agar solution has been poured into the bottom 12 the entire cell 10 including a container which comprise the bottom 12 and the top 16 and the agar-based gel 14, is autoclaved at a reasonably low temperature generally somewhat above 60° C for a sufficient time to ensure sterility of the eventually formed agar-based gel 14. Quite often, the solution from which the agar-based gel is to be formed is autoclaved prior to the addition thereto of some of the nutrients which are to be added thereto. Many variations from this basic process can and do occur and are well known in the art. Description of a number of such processes can be found for example in the Difco Manual, Ninth Edition, 1953, Difco Laboratories, Detroit. Since the present invention does not at all reside in any changes in these portions of the well known prior art process or in any changes in the normal nutrients used in an agar-based gel, such will not be discussed in further detail herein.

Turning to FIG. 2 there is illustrated very clearly a serious problem which occurs with prior art agar-based gels 14, namely the formation of a plurality of bubbles 18, some of which lead to the formation on a top surface 20 of the agar-based gel 14 of depressions 22 and/or hills 24. If one tries to grow a micro-organism upon a top surface 20 of an agar-based gel 14 having depressions 22 and/or hills 24 therein it is found that the growth rate of the micro-organism is not reproducible from one container or petri dish to another. Thus, it has been necessary to somehow treat the top surface 20 of the agar-based gel 14 which has depressions 22 and/or hills 24 therein due to bubbles 18 therein to somehow smooth the top surface 20. Generally, this has been accomplished by opening the cell 10 by taking off the top 16 therefrom and then directing a relatively low temperature flame upon the top surface 20 of the agar-based gel 14 to locally melt the agar-based gel 14 and thus smooth out the depressions 22 and/or hills 24. Contamination problems are thus introduced, the flaming takes a good deal of time, and even with a flamed top surface 20 one cannot be absolutely sure that each one of a plurality of cells 10 has an equally smooth top surface 20 on the agar-based gel 14 therein.

Turning now to FIG. 1 it will be seen that the cell 10 therein having the agar-based gel 14 therein has a top surface which is completely smooth and lacking in depressions 22 and hills 24. This is accomplished in accordance with the present invention by having intimately intermixed throughout the agar-based gel 14 a particular amount of one of a particular class of chemical compounds.

In accordance with the present invention from about 0.0008 to about 0.2 weight percent based on the total weight of the agar-based gel 14 of a dialkylpolysiloxane is intimately intermixed throughout the agar-based gel 14. The presence of the dialkylpolysiloxane causes the top surface 20 of the agar-based gel 14 to be smooth thus ensuring a generally reproducible growth rate for a micro-organism placed upon the top surface 20. The dialkylpolysiloxane must be such that it will itself in no way either accelerate or decelerate the growth of a micro-organism. Also, the dialkylpolysiloxane must be sufficiently dispersible within the agar-based solution from which the agar-based gel 14 is formed so that it can be intimately intermixed therewith and will stay generally intimately intermixed therewith during normal gel formation. Generally, the alkyl groups of the dialkylpolysiloxane will each be selected from a group of alkyl radicals consisting of methyl, ethyl, n-propyl, isopropyl, cyclopropyl, n-butyl, sec-butyl, t-butyl, cyclobutyl, and methylcyclopropyl. The most preferred dialkylpolysiloxane is dimethylpolysiloxane because of its ready availability, low cost and excellent properties when used in an agar-based gel 14.

Generally, the agar-based gel 14 will further include intimately intermixed therethroughout a non-ionic emulsifier to aid in the intermixing of the dialkylpolysiloxane with the solution from which the gel 14 is being formed. The non-ionic emulsifier will generally be present in an amount which falls within the range from about 0.0008 weight percent to about 2.0 weight percent of the gel. More preferably, the amount of the non-ionic emulsifier will fall within a range from about 0.008 weight percent to about 0.08 weight percent of the gel. The exact chemical nature of the non-ionic emulsifier is relatively unimportant. It is only necessary that said non-ionic emulsifier be non-toxic and non-growth rate effecting (growth rate of microorganisms). The preferred emulsifier of the present invention comprises a hydrophilic silica such as fumed silica or the like. Hydrophilic silica is a relatively low bulk density particulate powdery material capable of forming hydrogen bonds with water when dissolved therein. Generally, the hydrophilic silica will have a large surface area, usually of at least $100m^2/gram$, preferably falling within the range from $100m^2/gram$ to $500m^2/gram$ and most preferably falling within the range from about $150m^2/gram$ to about $250m^2/gram$. Commercially available fumed silica, made by decomposing $SiCl_4$ in the presence of water vapor (such as a product sold under the trademark Cabosil M-5 by Cabot Corporation, Boston, Mass.) is an especially useful form of hydrophilic silica. Hydrophilic silica of suitable properties can also be made by careful precipitation of silica from solution. Precipitated hydrophilic silica is available commercially, for example, from Philadelphia Quartz Company and is sold under the trademark QUSO. Further description of this type of hydrophilic silica and its preparation is found in U.S. Pat. No. 3,208,823.

The emulsifier preferably further comprises an alkyl cellulose coemulsifier such as methylcellulose, ethylcellulose, n-propylcellulose, isopropylcellulose, mixtures thereof or the like in an amount which generally falls within a range from about 0.0008 weight percent to about 1.0 weight percent, prefereably 0.001 to 0.5 weight percent based on total gel weight. Most preferably the further component of the emulsifier comprises methylcellulose.

It is further preferred that the solution from which the agar-based gel 14 is formed includes therewith sorbic acid. Generally, the sorbic acid will be present in an amount which falls within a range from about 0.0001 weight percent to about 1.0 weight percent of the gel. More preferably the amount of sorbic acid will fall within the range from about 0.001 weight percent to about 0.5 weight percent. The sorbic acid is believed to aid in the stability and storability of a premixed polysiloxane solution which comprises water and a non-ionic emulsifier such as hydrophilic silica plus methylcellulose.

The process of the present invention for growing the microorganism upon the top surface 20 of the agar-based nutrient containing gel 14 at a generally reproducible growth rate includes basically three steps. In the first step there is intermixed with agar, essential nutrients and water, sufficient of the agar being used to control formation of a gel, prior to the gelling thereof, from about 0.0008 to about 0.2 weight percent of a dialkylpolysiloxane as described above. More preferably the amount of dialkylpolysiloxane falls within the range from about 0.008 to about 0.08 weight percent. Each of these weights percent is based upon the total weight of the agar-based gel 14. It is impotant to the practice of the present invention that the intermixing occur at a temperature which is reasonably low. Generally, the temperature at which the intermixing occurs should fall within a range from about 0° C to about 80° C and more preferably from about 0° C to about 50° C. It is preferable although not essential that the dialkylpolysiloxane be intermixed with the water prior to intermixing of the agar therewith. This seems to result in maximum effectiveness of the dialkylpolysiloxane in insuring a smooth top surface 20 upon the agar-based gel 14.

In the second step of the process of the present invention the top surface 20 of the agar-based gel 14 is innoculated with a microorganism. This is generally carried out in a manner consistent with that which is old in the art. Thus, a swab infected with a microorganism can simply be touched against a spot on the top surface 20 of the gel. Alternatively, standard discs having particular microorganisms thereon may be contacted with the top surface 20 of the agar-based gel 14.

Finally, the cell 10 is incubated under preselected incubation conditions which are conducive to microorganism growth. It is of course understood that these conditions will vary somewhat depending upon the particular microorganism being grown. A typical incubation temperature might be 35° C and a typical incubation time might be 24 hours. It should clearly be recognized that fairly large variations in both this temperature and time of incubation can be used for the incubating step. The microorganisms then grow upon the smooth top surface 20 of the gel 14 at a generally reproducible growth rate.

A commercially available product, namely ANTI-FOAM C EMULSION, FOOD GRADE produced by DOW CORNING CORPORATION, MIDLAND, MICHIGAN, which commercial antifoam emulsion includes dimethylpolysiloxane, silica, methylcellulose, sorbic acid and the remainder water may very effectively be used to carry out the process of the present invention and to prepare growth cells in accordance with the present invention. Silicone defoamers have previously been used in defoaming any number of industrial processes including wine production, waste yeast tanks at breweries, fermentation processes, instant coffee production, soft drink production and the like. The uses of such silicone defoamers are set out in more detail in Bulletin 22-272 published by Dow Corning Corporation, Midland, Michigan in April of 1974.

The following examples illustrate the extremely unexpected results obtained when using the process of the present invention for growing a microorganism and the growth cell of the present invention for growing a microorganism. More particularly, the following examples demonstrate the unexpected result that the presence of a dialkylpolysiloxane in accordance with the present invention in an agar-based nutrient gel in no way effects the growth rates of a variety of microorganisms at a variety of concentrations and further that these growth rates are generally reproducible for each microorganism.

EXAMPLE 1

Trypticase (a trademark of BBL) Soy Agar was prepared which contained 0.025 weight percent of a 30% solution of dimethylpolysiloxane, silica, methylcellulose, sorbic acid, and the remainder water (about five drops of the aforesetout solution per liter of agar) was autoclaved at 121° centigrade for 20 minutes. The solution was cooled to approximately 50° centigrade and defibrinated sheep blood was added to a final concentration of 5% sheep blood. Aliquots of the solution were poured into four petri dishes and allowed to solidify. These four petri dishes are herein referred to as A, B, C and D. Simultaneously, a b 5% sheep blood agar plate was made from the same trypticase soy agar in the same manner but without the presence of the dimethylpolysiloxane, the silica, the methylcellulose, or the sorbic acid. The second solution was divided up into four aliquots each of which was poured into a petri dish, which four petri dishes are herein referred to as E, F, G and H.

Each of plates A–H was tested with Escherichia coli (ATCC 25922). Plates E–H were either selected to have a generally smooth top surface or, as necessary were flamed to have a smooth top surface. Plates A–D had a flat smooth top surface without flaming. Plates A and E were inoculated with E. coli obtained from Difco Bactro Discs Set A which had been diluted to one-tenth concentration and was plated on the media. Plates B and F were plated with the microorganism solution diluted 100 to 1, plates C and G were plated with a solution diluted 10,000 to 1 and plates D and H were plated with microorganism which was diluted 1,000,000 to 1. Inoculation of plate A was simultaneous with inoculation of plate E, inoculation of plate B was simultaneous with inoculation of plate F, inoculation of plate C was simultaneous with inoculation of plate G, and inoculation of plate D was simultaneous of plate H.

Each of the eight petri dishes A–H was incubated at 35° centigrade for 24 hours and the growth density was determined as read on a scale of 1 to 4. Table 1 summarizes the results obtained.

TABLE 1

| Dish Designation | Dilution | Density level |
| --- | --- | --- |
| A | $10^{-1}$ | 4.25 |
| B | $10^{-2}$ | 3.25 |
| C | $10^{-4}$ | 2.6 |
| D | $10^{-6}$ | 0.6 |
| E | $10^{-1}$ | 4.2 |
| F | $10^{-2}$ | 3.2 |
| G | $10^{-4}$ | 2.45 |
| H | $10^{-6}$ | 0.6 |

It is clear from the above data that an agar-based nutrient gel produced in accordance with the present invention shows no significant effects which could be construed as toxic, bacteriostatic, or bactericidal. The presence of the additive of the present invention in the agar-based nutrient medium appears from all evidence to be non-nutritive and provides absolutely no alterations to the visual and performance characteristics of the medium. It's usefulness in the elimination of bubbles leads to the formation of a smooth surface thereon whereby flaming is not required and high waste factors in manufacturing operations are greatly reduced. Visual observation of each of the dishes A–E reveal that they had a completely smooth top surface without the necessity for any flaming thereof.

EXAMPLE 2

Four additional petri dishes were prepared and labeled $A_1$, $B_1$, $C_1$, and $D_1$ with the contents of these four dishes being identical to those of the dishes A, B, C and D. Similarly, four additional petri dishes were prepared and labeled $E_1$, $F_1$, $G_1$, and $H_1$. The medium in these later four petri dishes was identical to the medium in petri dishes E, F, G, and H.

Testing proceeded just as example 1 with the exception that the test was carried out on *Salmonella typhimurium* which was prepared from a freshly isolated clinical specimen. The results of this testing is set out in table 2.

TABLE 2

| Dish Designation | Dilution | Density Level |
|---|---|---|
| $A_1$ | $10^{-1}$ | 4.3 |
| $B_1$ | $10^{-2}$ | 3.4 |
| $C_1$ | $10^{-4}$ | 2.75 |
| $D_1$ | $10^{-6}$ | 0.7 |
| $E_1$ | $10^{-1}$ | 4.15 |
| $F_1$ | $10^{-2}$ | 3.2 |
| $G_1$ | $10^{-4}$ | 2.65 |
| $H_1$ | $10^{-6}$ | 0.65 |

This example illustrates that an agar-based nutrient gel produced in accordance with the present invention shows no more effects which could be considered as toxic, bacteriostatic or bactericidal with *Salmonella typhimurium* as with *Escherichia coli*. Once again, the agar-based nutrient gel exhibited a completely smooth surface without the necessity for any flaming thereof.

EXAMPLE 3

This example was carried out identically to examples 1 and 2 with the exception that *Proteus vulgaris* (ATCC 6380) was the microorganism used for inoculation rather than either *Escherichia coli* or *Salmonella typhimurium*. Eight equivalent petri dishes were prepared to those prepared in example 1 and these were labeled respectively $A_2$, $B_2$, $C_2$, $D_2$, $E_2$, $F_2$, $G_2$, $H_2$. Table 2 summarizes the data obtained on growth density with *Proteus vulgaris*.

TABLE 3

| Dish Designation | Dilution | Density Level |
|---|---|---|
| $A_2$ | $10^{-1}$ | 4.65 |
| $B_2$ | $10^{-2}$ | 3.4 |
| $C_2$ | $10^{-4}$ | 2.25 |
| $D_2$ | $10^{-6}$ | 0.6 |
| $E_2$ | $10^{-1}$ | 4.4 |
| $F_2$ | $10^{-2}$ | 3.35 |
| $G_2$ | $10^{-4}$ | 2.15 |
| $H_2$ | $10^{-6}$ | 0.65 |

This example illustrates that an agar-based nutrient gel in accordance with the present invention once again has no effects which could be construed as toxic, bacteriostatic, or bactericidal with respect to *Proteus vulgaris*. Once again, the petri dishes prepared with an agar-based nutrient medium in accordance with the present invention exhibited a completely smooth top surface.

EXAMPLE 4

This example was carried out in complete conformance with examples 1-3 with the exception that *Streptococcus pyogenes* was used instead of *Escherichia coli*, *Salmonella typhimurium*, or *Proteus vulgaris*. The *Streptococcus pyogenes* was obtained from freshly isolated clinical specimens obtained from a laboratory. Eight petri dishes were prepared as before and were in this case labeled $A_3$, $B_3$, $C_3$, $D_3$, $E_3$, $F_3$, $G_3$, and $H_3$. The results of the testing are summarized in table IV.

TABLE IV

| Dish Designation | Dilution | Density Level |
|---|---|---|
| $A_3$ | $10^{-1}$ | 4.65 |
| $B_3$ | $10^{-2}$ | 3.45 |
| $C_3$ | $10^{-4}$ | 2.1 |
| $D_3$ | $10^{-6}$ | 0.6 |
| $E_3$ | $10^{-1}$ | 4.6 |
| $F_3$ | $10^{-2}$ | 3.45 |
| $G_3$ | $10^{-4}$ | 2.1 |
| $H_3$ | $10^{-6}$ | 0.65 |

This example illustrates that no effects are observed which should be considered as toxic, bacteriostatic, or bactericidal when the microorganism grown on the gel in the petri dish was *Streptococcus pyogenes*. Once again, the agar-based nutrient gels in each of the four petri dishes prepared in accordance with the present invention exhibited completely smooth surfaces without the necessity for any flaming.

The above four examples together illustrate that no effects which could be construed as toxic, bacteriostatic or bactericidal occur when an agar-based nutrient gel is prepared in accordance with the present invention and when a wide variety of microorganisms are grown thereon.

EXAMPLE 5

A plurality of samples of each of *Escherichia coli*, *Salmonella typhimurium*, *Proteus vulgaris*, and *Streptococcus pyogenes* are each grown on agar-based nutrient gels within respective petri dishes with the gels being made in accordance with the present invention and generally prepared as described in example 1. For each of the *Escherichia coli* at a given concentration the growth rate in each petri dish is reproducibly the same. Similar results are obtained with *Salmonella typhimurium*, *Proteus vulgaris* and *Streptococcus pyogenes*.

This example illustrates the reproducibility of growth rate of a wide variety of microorganism in equal concentration on different agar-based nutrient gels, each of which is made in accordance with the present invention and contains the same nutrient concentration therein.

While the invention has been described in connection with specific embodiments thereof, it will be understood that it is capable of further modification, and this application is intended to cover any variations, uses or adaptations of the invention following, in general, the principles of the invention and including such departures from the present disclosure as come within known or customary practice in the art to which the invention pertains and as may be applied to the essential features hereinbefore set forth, and as fall within the scope of the invention and the limits of the appended claims.

That which is claimed is:

1. A process for growing a microorganism upon the surface of an agar-based nutrient gel without substantially effecting the rate of growth of microorganisms grown thereon, comprising:

intermixing with agar, essential nutrients and water, sufficient of said agar being used to insure formation of a gel, and, from about 0.0008 to about 0.2 weight percent of a dialkylpolysiloxane based on total gel weight;

gelling the resulting intermixture in a microorganism growth container to form a growth cell with a completely smooth top surface on the gel therein;

inoculating the smooth top surface of said gel with a bacterial microorganism; and incubating said cell under preselected incubation conditions to grow said bacterial microorganisms upon the smooth top surface of the gel at substantially the same rate of growth as occurs on a completely smooth surface of an otherwise identical gel lacking said dialkylpolysiloxane.

2. A process as in claim 1, wherein said intermixing occurs at a temperature which falls within a range from about 0° C to about 80° C.

3. A process as in claim 2, wherein said intermixing occurs at a temperature which falls within a range from about 0° C to about 50° C.

4. A process as in claim 2, wherein said dialkylpolysiloxane is intermixed with said water prior to the intermixing of said agar therewith.

5. A process as in claim 2, wherein said dialkylpolysiloxane is in the form of an emulsion in water, said emulsion including sufficient of a non-toxic, non-growth rate effecting emulsifying agent to maintain said dialkylpolysiloxane suspended in said water.

6. A process as in claim 5, wherein said emulsifying agent comprises a non-ionic emulsifier.

7. A process as in claim 6, wherein said alkyl groups of said dialkylpolysiloxane are each selected from the group consisting of methyl, ethyl, n-propyl, isopropyl, cyclopropyl, n-butyl, sec-butyl, t-butyl, cyclobutyl, and methylcyclopropyl.

8. A process as in claim 7, wherein said emulsifier comprises a hydrophilic silica.

9. A process as in claim 8, wherein said emulsifier further comprises methylcellulose.

10. A process as in claim 9, wherein said solution further includes sorbic acid.

11. A process as in claim 10, wherein said alkyl groups are both methyl groups.

12. A microorganism growth cell, comprising:
a sterilized container;
an agar-based nutrient gel within said container, said gel having intimately intermixed therethroughout from about 0.0008 to about 0.2 weight percent of a dialkylpolysiloxane which causes a top surface of the gel to be smooth insuring a uniform growth rate for a bacterial microorganism placed upon said top surface, said rate of growth being substantially the same rate as occurs on a substantially smooth top surface of an otherwise identical gel lacking said dialkylpolysiloxane.

13. A cell as in claim 12, wherein said gel further includes intimately intermixed therethroughout a non-toxic, non-growth rate effecting, non-ionic emulsifier in an amount which falls within a range from about 0.0008 weight percent to about 2.0 weight percent of said gel.

14. A cell as in claim 13, wherein the alkyl groups of said dialkylpolysiloxane are each selected from the group consisting of methyl, ethyl, n-propyl, isopropyl, cyclopropyl, n-butyl, sec-butyl, t-butyl, cyclobutyl and methylcyclopropyl.

15. A cell as in claim 14, wherein said emulsifier comprises a hydrophilic silica.

16. A cell as in claim 15, wherein said emulsifier further comprises methylcellulose.

17. A cell as in claim 16, wherein said gel further includes sorbic acid.

18. A cell as in claim 17, wherein said alkyl groups are both methyl groups.

19. A method of preventing bubble formation in an agar-based nutrient medium without substantially effecting the rate of growth of bacterial microorganisms grown on gels made therefrom, comprising including in a solution of agar in water prior to the gelling thereof from about 0.0008 to about 0.2 weight percent of a dialkylpolysiloxane based on total gel weight, water and sufficient of a non-toxic, non-growth effecting emulsifying agent to maintain said dialkylpolysiloxane suspended in said water, said bacterial microorganisms growing on said gels at substantially the same rate of growth as occurs on completely smooth top surfaces of otherwise identical gels lacking said dialkylpolysiloxane.

20. A method as in claim 19, wherein said emulsifying agent comprises a non-ionic emulsifier.

21. A method as in claim 20, wherein said alkyl groups of said dialkylpolysiloxane are each selected from the group consisting of methyl, ethyl, n-propyl, isopropyl, cyclopropyl, n-butyl, sec-butyl, t-butyl, cyclobutyl and methylcyclopropyl.

22. A method as in claim 21, wherein said emulsifier comprises a hydrophilic silica.

23. A method as in claim 22, wherein said emulsifier further comprises methylcellulose.

24. A method as in claim 23, wherein said solution further includes sorbic acid.

25. A method as in claim 24, wherein said alkyl groups are both methyl groups.

* * * * *